United States Patent
Zou et al.

(10) Patent No.: US 12,076,416 B2
(45) Date of Patent: Sep. 3, 2024

(54) GENE EDITING NANOCAPSULE AND PREPARATION METHOD AND USE THEREOF

(71) Applicant: Henan University, Kaifeng (CN)

(72) Inventors: Yan Zou, Kaifeng (CN); Bingyang Shi, Kaifeng (CN); Meng Zheng, Kaifeng (CN); Xinhong Sun, Kaifeng (CN)

(73) Assignee: Henan University, Kaifeng (CN)

( * ) Notice: Subject to any disclaimer, the term of this patent is extended or adjusted under 35 U.S.C. 154(b) by 239 days.

(21) Appl. No.: 17/675,556

(22) Filed: Feb. 18, 2022

(65) Prior Publication Data

US 2022/0323605 A1  Oct. 13, 2022

(30) Foreign Application Priority Data

Mar. 10, 2021 (CN) .......................... 202110260752.1

(51) Int. Cl.
| | |
|---|---|
| A61K 47/69 | (2017.01) |
| A61K 38/46 | (2006.01) |
| A61P 35/00 | (2006.01) |
| C12N 11/04 | (2006.01) |
| C12N 15/11 | (2006.01) |

(52) U.S. Cl.
CPC ........ *A61K 47/6925* (2017.08); *A61K 38/465* (2013.01); *A61P 35/00* (2018.01); *C12N 15/11* (2013.01); *C12N 11/04* (2013.01); *C12N 2310/20* (2017.05); *C12N 2310/351* (2013.01); *C12N 2310/3513* (2013.01)

(58) Field of Classification Search
CPC .............. A61K 47/6925; A61K 38/465; A61K 31/7105; A61K 47/58; A61K 47/62; A61K 48/0041; A61P 35/00; C12N 15/11; C12N 11/04; C12N 2310/20; C12N 2310/351; C12N 2310/3513; C12N 9/22; C12N 15/113; Y02A 50/30; B82Y 5/00; B82Y 30/00; B82Y 40/00; C08F 283/065
See application file for complete search history.

(56) References Cited

U.S. PATENT DOCUMENTS

2021/0322330 A1* 10/2021 Shi .................. C12N 15/111

FOREIGN PATENT DOCUMENTS

WO  WO-2020139807 A2 *  7/2020 ............. A61K 35/28

OTHER PUBLICATIONS

Wu, Jun, et al. "Hydrophobic cysteine poly (disulfide)-based redox-hypersensitive nanoparticle platform for cancer theranostics." Angewandte Chemie 127.32 (2015): 9350-9355. (Year: 2015).*
Eoh, Joon, and Luo Gu. "Biomaterials as vectors for the delivery of CRISPR-Cas9." Biomaterials science 7.4 (2019): 1240-1261. (Year: 2019).*
Li, Minghui, et al. "Functional nanoparticles in targeting glioma diagnosis and therapies." Journal of nanoscience and nanotechnology 14.1 (2014): 415-432. (Year: 2014).*
GenBank No. KJ905273.1 (Year: 2015).*

* cited by examiner

*Primary Examiner* — Paul J Holland
*Assistant Examiner* — Erica Nicole Jones-Foster

(57) ABSTRACT

The present disclosure provides a gene editing nanocapsule and a preparation method and use thereof. The gene editing nanocapsule has a core-shell structure, wherein the inner core includes a Cas/sgRNA ribonucleoprotein complex, and the outer shell includes a polymer, the Cas/sgRNA ribonucleoprotein complex has a gene editing function, and the polymer acts as a carrier for the Cas/sgRNA ribonucleoprotein complex and protects it, because the polymer contains tumor microenvironment sensitive molecules, the nanocapsules can be efficiently released in tumor cells. Further, the surface of the outer shell can be modified with a targeting agent, so that the nanocapsule can specifically target tumor cells, which improves the endocytosis efficiency of the nanocapsule. The gene editing nanocapsule has good biocompatibility and biosafety, and is expected to become a safe and efficient gene therapy drug for tumors.

17 Claims, 13 Drawing Sheets

Specification includes a Sequence Listing.

GENE EDITING NANOCAPSULE AND PREPARATION METHOD AND USE THEREOF

CROSS-REFERENCE TO RELATED APPLICATIONS

The present disclosure claims priority to Chinese Patent Application No. 2021102607521, filed with the Chinese Patent Office on Mar. 10, 2021, entitled "Gene Editing Nanocapsule and Preparation Method and Use Thereof", which is incorporated herein by reference in its entirety.

REFERENCE TO A SEQUENCE LISTING

This application includes a Substitute Sequence Listing filed electronically as a text file named Substitute Sequence Listing_CHOFN-24036-USPT.txt, created on Mar. 13, 2024, with a size of 2,558 bytes. The Substitute Sequence Listing is incorporated herein by reference.

TECHNICAL FIELD

The present disclosure relates to the technical field of gene editing, in particular to a gene editing nanocapsule, and a preparation method and use thereof.

BACKGROUND ART

Malignant tumors are the primary disease threatening human life and health. Most tumors have an insidious onset, and the early symptoms are not obvious, at the time of diagnosis, it has already been in the middle and late stages, and the opportunity for surgical resection is lost. At present, chemotherapy is still one of the main methods of tumor treatment. However, traditional chemotherapeutic drugs have strong toxic and side effects, poor targeting, and are prone to drug resistance. Because gene therapy can specifically change genetic material to achieve the purpose of treatment, it has characteristics of strong targeting, small toxic and side effects and permanent treatment, and plays an increasingly important role in tumor treatment, but also faces defects such as complicated operation, low efficiency, and insufficient application range.

In recent years, gene editing technology has provided a new approach to the deficiencies in the field of gene therapy. Among them, the CRISPR-Cas9 genome editing system is highly efficient, can edit multiple genes at the same time, is simple to operate, and has a wide range of applications. It plays a pivotal role in the field of gene therapy. This system is part of the adaptive immune system in archaea and bacteria, which protects against the invasion of phages and plasmids. Two key components, Cas9 nuclease and sgRNA, are essential for CRISPR/Cas9 activity. Among them, sgRNA recognizes the target sequence in the genome and guides Cas9 nuclease to the target sequence, the Cas9 nuclease in the system acts as a scissors to cut the double strands of DNA, and then by the in vivo double-strand break repairing system: non-homologous end joining (NHEJ) or homologous recombination repair (HDR), the target sequence is changed, thereby realizing gene editing. Since it is discovered, CRISPR-Cas9 has become the most powerful eukaryotic gene editing engineering, which has aroused great interest in tumor treatment. At present, this system has been widely used in tumor research.

Although the CRISPR-Cas9 technology has a bright future, some challenges still need to be solved. The biggest challenge is how to safely and efficiently targetedly deliver the CRISPR-Cas9 genome editing system into tumor cells. One of the delivery methods is to encapsulate Cas9 and sgRNA into viral vectors in the form of plasmids. However, in this way, plasmid DNA can be randomly integrated into the genome, causing cancer or other genetic diseases. In addition, the template-driven expression of genes limits the control of the total amount of Cas9, and the off-target of this system is mainly due to overdosing.

An alternative delivery method is to deliver the Cas9/sgRNA ribonucleoprotein complex, which allows better control of its intracellular concentration and limits the time range in which the gene editing can be carried out. However, drug delivery still faces huge challenges. Most proteins, such as enzymes, antibodies, or transcription factors or the like, face the problems of low stability and poor cell membrane permeability due to their fragile tertiary structure and large molecular size. RNA has a strong negative charge, does not easily penetrate cell membranes, and is sensitive to nucleases, and usually requires chemical modification to prevent degradation. Therefore, it is necessary to design a suitable carrier to prevent the harmful physiological environment from destroying protein and RNA, and deliver both into target cells at the same time.

In recent years, the rapid development of nanotechnology in the medical field has brought new opportunities for tumor treatment. The size of nanoparticles ranges from tens to hundreds of nanometers, nanoparticles can be designed to encapsulate and deliver genetic material and the like. High surface area ratio, small volume, loadable for various drugs, modifiable property and other properties endow nanomaterials with advantages that other materials cannot match in tumor treatment, for example, enhancing biocompatibility, tumor targeting, prolonging the cycle time of the drug in the blood, controlling drug release, carrying multiple drugs for combined therapy and the like. By enhanced permeability and retention effect (EPR) effect (that is, the permeability of the blood vessel at the tumor site is larger than that of the normal blood vessel, and the nanodrug cannot easily penetrate the normal blood vessel but can pass through the tumor blood vessel), more nanodrugs are targetedly concentrated in tumor tissues and the damage to normal tissues is reduced.

SUMMARY

The purpose of the present disclosure is to provide a gene editing nanocapsule and a preparation method and use thereof. The gene editing nanocapsule contains a Cas/sgRNA ribonucleoprotein complex and uses a polymer to carry and protect it, the gene editing nanocapsule can be efficiently released in tumor cell and is expected to become a safe and efficient gene therapy drug for tumors.

To achieve the above purpose, the present disclosure first provides a gene editing nanocapsule, which comprises an inner core and an outer shell encapsulating the inner core, wherein the inner core comprises a Cas/sgRNA ribonucleoprotein complex obtained by combining Cas nuclease and sgRNA; and the outer shell comprises a polymer polymerized by a monomer material, wherein the monomer material comprises a first monomer and a second monomer that may be polymerized with each other, wherein the first monomer is a molecule capable of electrostatically binding with the Cas/sgRNA ribonucleoprotein complex, and the second monomer is a tumor microenvironment sensitive molecule.

Specifically, the particle size of the gene editing nanocapsule is 30-50 nm, and the particle size is smaller, thereby having a higher cell endocytosis efficiency.

In some embodiments of the present disclosure, the first monomer comprises at least one of guanidino acrylate, spermine acrylate, and N-(3-aminopropyl) methacrylamide; and the tumor microenvironment sensitive molecule comprises at least one of reduction-sensitive molecules, acid-sensitive molecules and ROS (active oxygen) responsive molecules; preferably, the second monomer is a reduction-sensitive molecule.

Optionally, the reduction-sensitive molecule is a molecule containing disulfide bond; preferably, the reduction-sensitive molecule is N,N'-bis(acryloyl) cystamine. Specifically, the structural formula of the N,N'-bis(acryloyl) cystamine is

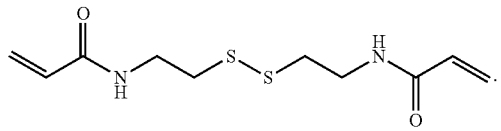 [SMILES: C=CC(=O)NCCSSCCNC(=O)C=C]

Specifically, the acrylate molecule in the acrylate polyethylene glycol succinimidyl formate contains double bonds and can participate in the polymerization reaction, and the acrylate polyethylene glycol succinimidyl formate contains polyethylene glycol molecules, polyethylene glycol (PEG) is a low-toxic water-soluble molecule that can shield the surface charge of nanoparticles, and also provide steric hindrance, which can reduce non-specific adsorption and aggregation, and can significantly enhance the stability of nanoparticles and increase the half-life of systemic circulation of the nanoparticles. The succinimidyl formate molecule in the acrylate polyethylene glycol succinimidyl formate can be connected to the targeting agent obtained by amination treatment through a chemical bond, so as to realize the connection between the polymer and the targeting agent.

Specifically, the structural formula of the acrylate polyethylene glycol succinimidyl formate is

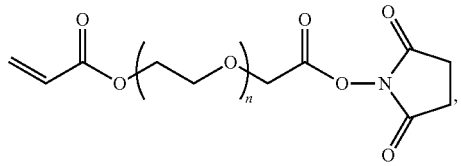

wherein n=22-120.

Specifically, since N,N'-bis(acryloyl)cystamine contains disulfide bonds, and GSH can break the disulfide bonds, and the GSH content in tumor tissues is much higher than the GSH content in normal tissues, after the gene nanocapsules prepared by the present disclosure enter the tumor cells, the polymer in them can be efficiently degraded by GSH, so that the release efficiency of the effective ingredient (Cas/sgRNA ribonucleoprotein complex) in gene nanocapsules in tumor cells is much higher than its release efficiency in normal cells, achieving the effect of the targeted release to the tumor cells, when the gene targeted by sgRNA is a tumor treatment target site, the effect of tumor cell death and normal cell survival can be achieved.

Specifically, since the guanidino acrylate is positively charged, it can be electrostatically bind to the negatively charged Cas/sgRNA ribonucleoprotein complex, so that the polymer is formed on the outer surface of the Cas/sgRNA ribonucleoprotein complex, and the guanidino acrylate can also increase the positive charge content of the entire nanocapsule, since the outer surface of the cell membrane is negatively charged, adding guanidino acrylate to the nanocapsule can improve the cell endocytosis efficiency of the nanocapsule.

Specifically, the structural formula of the guanidino acrylate is

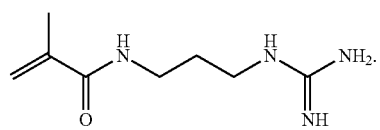

In some embodiments of the present disclosure, the gene editing nanocapsule further comprises a targeting agent modified on the outer surface of the outer shell; the monomer material further comprises a third monomer that may be polymerized with the first monomer and/or the second monomer, wherein the third monomer is a molecule that may be connected to the targeting agent through a chemical bond.

Optionally, the third monomer comprises at least one of acrylate polyethylene glycol succinimidyl formate and acrylate polyethylene glycol maleimide.

Optionally, the targeting agent comprises at least one of Angiopep-2, RGD peptide, apolipoprotein E, and transferrin; preferably, the targeting agent is Angiopep-2.

Specifically, Angiopep-2 can not only be used as a targeting agent to specifically target tumor cells, so as to improve the endocytosis efficiency of nanocapsules, but also has a mediating effect, and can mediate nanocapsules to span BBB, so that the nanocapsules are efficiently swallowed by human glioma (brain glioma) cells.

The existence of the blood brain barrier (BBB) makes human glioma become one of the most difficult tumors in cancer treatment. BBB is the self-balancing defense mechanism of the brain, on the one hand, it ensures that the central nervous system is protected from invasion of the foreign substances, maintaining an efficient homeostasis, and at the same time inputs nutrients into the brain; on the other hand, the dense structure of BBB also prevents therapeutic drugs from entering the brain through non-invasive administration. Because BBB endothelial cells and GBM (glioblastoma multiforme) tissues both highly express receptor-related protein 1 (LRP-1), when applying the gene editing nanocapsules provided by the present disclosure to treat GBM, the targeting agent is preferably Angiopep-2, Angiopep-2 (NH$_2$) modified gene editing nanocapsules can specifically bind to the low-density lipoprotein (LRP) receptor overexpressed on brain endothelial cells and glioma cells, which can significantly enhance the BBB permeability of the Cas/sgRNA ribonucleoprotein complex, while targeting the glioma cells.

Optionally, the target gene of the sgRNA is a tumor-targeted therapeutic gene; optionally, the tumor-targeted therapeutic gene comprises at least one of the MTH1 gene and the PLK1 gene; optionally, the sequence of the target site of the sgRNA on the PLK1 gene is shown in SEQ ID NO:1.

Optionally, the Cas nuclease is Cas9 nuclease.

In some embodiments of the present disclosure, the molar ratio of the Cas nuclease and the sgRNA is 1:1 to 1.5, preferably 1:1.2;

the monomer material comprises acrylate polyethylene glycol succinimidyl formate, guanidino acrylate, and N,N'-bis(acryloyl)cystamine, the molar ratio of acrylate polyethylene glycol succinimidyl formate, guanidino acrylate, and N,N'-bis(acryloyl) cystamine is 1~3:1~3:1~3, preferably 1:1:1; the molar ratio of Cas nuclease and guanidino acrylate is 1:200~250, preferably 1:220;

the targeting agent is Angiopep-2, and the molar ratio of Angiopep-2 and acrylate polyethylene glycol succinimidyl formate is 1~5:1, preferably 3:1.

The present disclosure also provides use of the gene editing nanocapsules in the preparation of drugs for treating tumors.

Optionally, the tumor is glioma, non-small cell lung cancer or cervical cancer; preferably, the tumor is glioma, more preferably, glioblastoma.

The present disclosure also provides a drug for treating tumors, which comprises the gene editing nanocapsule.

Optionally, the tumor is glioma, non-small cell lung cancer or cervical cancer; preferably, the tumor is glioma, more preferably, glioblastoma.

The present disclosure also provides a preparation method of the gene editing nanocapsule, which includes the following steps:

step 1. incubating Cas nuclease and sgRNA in a buffer to form a Cas/sgRNA ribonucleoprotein complex; and step 2. adding the monomer material and the initiator to the system obtained in step 1, so that the monomer material undergoes a polymerization reaction to form the polymer that is coated on the outer surface of the Cas/sgRNA ribonucleoprotein complex.

In some embodiments of the present disclosure, the preparation method further comprising: step 3. adding a targeting agent to the system obtained in step 2, wherein the targeting agent is connected to the polymer by a chemical bond.

Optionally, the targeting agent comprises at least one of Angiopep-2, RGD peptide, apolipoprotein E, and transferrin; preferably, the targeting agent is Angiopep-2.

Optionally, in step 3, after adding the targeting agent, the resultant was stirred for 1 to 3 hours.

The monomer material added in the step 2 further comprises a third monomer that may be polymerized with the first monomer and/or the second monomer, wherein the third monomer is a molecule that may be connected to the targeting agent through a chemical bond.

Optionally, the third monomer comprises at least one of acrylate polyethylene glycol succinimidyl formate and acrylate polyethylene glycol maleimide.

Optionally, the initiator comprises ammonium persulfate and N, N, N',N'-tetramethylethylenediamine, the ratio of ammonium persulfate and reaction system is 1~5 mg:500 µL, the ratio of N,N,N',N'-tetramethylethylenediamine solution and reaction system is 1~5 µL: 500 µL, and the concentration of N,N, N',N'-tetramethylethylenediamine solution is 0.2%-0.8% w/v.

Optionally, the step 1 is performed under the condition of 10° C.~30° C., and the incubation time is 3 to 8 minutes; the step 2 is performed at 0° C.~5° C. in an oxygen-free environment with stirring, and the reaction time is 60 to 120 minutes.

Optionally, the preparation method of the gene editing nanocapsule further comprises: after the gene editing nanocapsules are prepared, a step of removing impurities is performed; optionally, an ultrafiltration centrifuge tube with a 10 kDa molecular weight cut-off is used for removing impurities.

It is understandable that the reason why the step 2 is performed under the condition of 0° ° C. to 5° C. is to avoid the heat released by the polymerization reaction that causes the system temperature to be too high, which leads to the inactivation of Cas nuclease.

Optionally, the step 2 is performed at the condition of 4°C.

Optionally, the stirring speed in the step 2 is 250-350 rpm.

It is understandable that since oxygen may hinder the progress of the polymerization reaction and cause the polymerization effect to deteriorate, step 2 is carried out in an oxygen-free environment.

Optionally, the oxygen-free environment is a nitrogen environment or an inert gas (helium, neon, argon, krypton, xenon) environment.

The beneficial effects of the present disclosure is as follows.

the gene editing nanocapsule of the present disclosure has a core-shell structure, wherein the inner core includes a Cas/sgRNA ribonucleoprotein complex, and the outer shell includes a polymer, the Cas/sgRNA ribonucleoprotein complex has a gene editing function, and the polymer acts as a carrier for the Cas/sgRNA ribonucleoprotein complex and protects it, because the polymer contains tumor microenvironment sensitive molecules, the nanocapsules can be efficiently released in tumor cells.

Further, the surface of the outer shell can be modified with a targeting agent, so that the nanocapsule can specifically target tumor cells, which improves the endocytosis efficiency of the nanocapsule.

The gene editing nanocapsule of the present disclosure has good biocompatibility and biosafety, and is expected to become a safe and efficient gene therapy drug for tumors.

The preparation method of the gene editing nanocapsule provided by the present disclosure has simple preparation process, high encapsulation efficiency, small particle size of the prepared nanocapsules, and high cell endocytosis efficiency.

BRIEF DESCRIPTION OF DRAWINGS

In order to illustrate the technical solutions of the embodiments of the present disclosure more clearly, the drawings need to be used in the embodiments will be briefly introduced below, it should be understood that the following drawings only show some embodiments of the present disclosure, and therefore should not be regarded as a limitation of the scope of the present disclosure.

FIG. 1A and FIG. 1B show the particle size distribution and morphological characteristics of $ANC_{SS}$ (Cas9/sgRNA) nanocapsules, wherein FIG. 1A is the particle size distribution diagram of $ANC_{SS}$ (Cas9/sgRNA) nanocapsules, FIG. 1B is a scanning electron micrograph of $ANC_{SS}$ (Cas9/sgRNA) nanocapsules.

FIG. 2A-FIG. 2E shows the experiment results of part of in vitro cells, wherein

FIG. 2A a flow cytometry diagram of $ANC_{SS}$ (Cas9/sgRNA) nanocapsules, ANC (Cas9/sgRNA) nanocapsules, $NC_{SS}$ (Cas9/sgRNA) nanocapsules, and Free Cas9/sgRNA after incubating for 4 hours in U87MG-luc cells;

FIG. 2B laser confocal micrograph of $ANC_{SS}$ (Cas9/sgRNA) nanocapsules, ANC (Cas9/sgRNA) nanocapsules, NC$_{SS}$ (Cas9/sgRNA) nanocapsules, and Free Cas9/sgRNA after incubating for 4 hours in U87MG-luc cells;

FIG. 2C T7E1 experiment analyzes the editing efficiency in U87MG-luc cells, and the values are obtained by imageJ analysis;

FIG. 2D WB analyzes the expression of PLK1 in U87MG-luc cells;

FIG. 2E sequencing results of PLK1 gene editing in U87MG-luc cells treated with ANC$_{SS}$ (Cas9/sgRNA) nanocapsules; FIG. 2E discloses SEQ ID NOs: 2-7, respectively, in order of appearance.

FIG. 3B WB analyzes the expression of PLK1 in CSC2-luc cells.

FIG. 4A, FIG. 4B and FIG. 4C are in vivo experimental study results, wherein

FIG. 4A shows the pharmacokinetic study of ANC$_{SS}$ (Cas9/sgRNA) nanocapsules, ANC (Cas9/sgRNA) nanocapsules, NC$_{SS}$ (Cas9/sgRNA) nanocapsules, and Free Cas9/sgRNA;

FIG. 4B shows the qualitative distribution of ANC$_{SS}$ (Cas9/sgRNA) nanocapsules, ANC (Cas9/sgRNA) nanocapsules, NC$_{SS}$ (Cas9/sgRNA) nanocapsules, and Free Cas9/sgRNA in the heart, liver, spleen, lung, and kidney; the enlarged image on the right shows the tumor penetration condition of ANC$_{SS}$ (Cas9/sgRNA) and the control group observed through a confocal laser scanning microscope (CLSM);

FIG. 4C shows the quantitative distribution of ANC$_{SS}$ (Cas9/sgRNA) nanocapsules, ANC (Cas9/sgRNA) nanocapsules, NC$_{SS}$ (Cas9/sgRNA) nanocapsules, and Free Cas9/sgRNA in the heart, liver, spleen, lung, and kidney.

FIG. 5B relative photon quantity of different nanoparticles;

FIG. 5C changes in body weight of mice during treatment;

FIG. 5D bioluminescence of U87MG-luc;

FIG. 5E survival rate of mice during treatment;

FIG. 5F T7E1 experiment analyzes the editing efficiency for U87MG-luc tumor tissue, and the values are obtained through imageJ analysis;

FIG. 5G H&E whole brain scanning to characterize tumor size;

FIG. 5H WB analyzes the expression of PLK1 in U87MG-luc tumor tissue;

FIG. 5I WB quantitative results;

FIG. 5J gene editing and sequencing results of U87MG-luc tumor tissue; FIG. 5J discloses SEQ ID NOs: 2, 8, 9, 4, 10, and 11, respectively, in order of appearance.

FIG. 6B biofluorescence of CSC2-luc cells;

FIG. 6C H&E whole brain scanning to characterize tumor size;

FIG. 6D relative photon quantity of different nanoparticles;

FIG. 6E changes in body weight of mice during treatment;

FIG. 6F survival rate of mice during treatment;

FIG. 6G T7E1 experiment analyzes the editing efficiency for CSC2-Luc tumor tissue, and the values are obtained by imageJ analysis;

FIG. 6H WB analyzes the expression of PLK1 in CSC2-Luc tumor tissues;

FIG. 6I WB quantitative results;

FIG. 6J gene editing and sequencing results of CSC2-Luc tumor tissue; FIG. 6J discloses SEQ ID NOs: 2, 3, 12, 4, and 13, respectively, in order of appearance.

DETAILED DESCRIPTION OF EMBODIMENTS

Figure 1A:
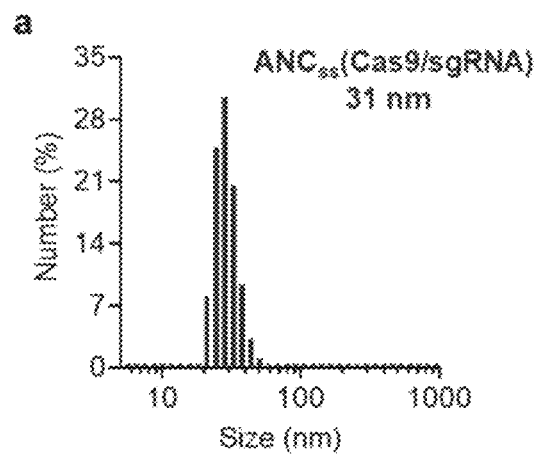

Terms as Used in the Present Disclosure

"Prepared from" is synonymous with "comprising". The terms "comprising", "including", "having", "containing" or any other variations as used herein are intended to cover non-exclusive inclusion. For example, the composition, step, method, product or device comprising the listed elements is not necessarily only limited to those elements, but may include other elements not explicitly listed or elements inherent to such composition, step, method, product, or device.

The conjunction "consisting of" excludes any unspecified elements, steps or components. If used in a claim, this phrase will make the claim closed so that it does not include materials other than those described, except for the conventional impurities associated with it. When the phrase "consisting of" appears in a clause of the subject of a claim rather than immediately after the subject matter, it is only limited to the elements described in the clause; other elements are not excluded from the claims as a whole.

When amount, concentration, other value or parameter is expressed in ranges, preferred ranges, or ranges defined by a series of upper limit preferred values and lower limit preferred values, this should be understood as specifically disclosing all ranges formed by any pairing of the upper limit or preferred value of any range and the lower limit or preferred value of any range, regardless of whether the ranges are separately disclosed. For example, when the range "1~5" is disclosed, the described range should be interpreted as including the ranges "1~4", "1~3", "1~2", "1~2 and 4~5", "1~3 and 5" and the like. When a numerical range is described herein, unless otherwise stated, the range is intended to include its end values and all integers and fractions within the range.

In these embodiments, unless otherwise specified, the parts and percentages mentioned are based on mass.

"Parts by mass" refers to the basic measurement unit that represents the mass ratio relationship of multiple components. 1 part can represent any unit mass, such as 1 g, or 2.689 g. If we say that the parts by mass of component A is a part, and the parts by mass of component B is b part, it means the ratio of the mass of component A to the mass of component B is a:b. Or, it means that the mass of component A is aK and the mass of component B is bK (K is an arbitrary number and represents a multiplying factor). It should not be misunderstood that, unlike the mass fraction, the sum of parts by mass of all components is not limited to 100 parts.

"And/or" is used to indicate that one or both of the stated conditions may occur, for example, A and/or B includes (A and B) and (A or B).

The implementation plan of the present disclosure will be described in detail below in conjunction with specific embodiments, but those skilled in the art will understand that the following embodiments are only used to illustrate the present disclosure and should not be regarded as limiting the scope of the present disclosure. If specific conditions are not indicated in the embodiments, it shall be carried out in accordance with the conventional conditions or the conditions recommended by the manufacturer. The reagents or instruments used without the manufacturer are all conventional products that can be purchased on the market.

The sources of some reagents used in the embodiments of the present disclosure are as follows.

Guanidino acrylate was synthesized by using the method described in the literature of ROS-Responsive Polymeric siRNA Nanomedicine Stabilized by Triple Interactions for the Robust Glioblastoma Combinational RNAi Therapy;

dipropylene cystamine (sigma);

acrylate polyethylene glycol succinimidyl formate (Jenkem); and

Angiopep-2 (ChinaPeptides).

In the embodiments of the present disclosure, room temperature refers to a temperature condition of 10° ° C. to 30° C.

(1) Synthesis of Nanocapsules

Example 1 Preparation Method of $ANC_{SS}$ (Cas9/sgRNA) Nanocapsules

Step 1. Cas9 and sgRNA were added to 500 µl 4-(2-hydroxyethyl)-1-piperazine ethanesulfonic acid (HEPES buffer) (10 mM PH 7.4) at a molar ratio of 1:1.2, and incubated at room temperature for 5 minutes.

Specifically, the target gene of the sgRNA is the PLK1 gene, and the sequence of the target site of the sgRNA on the PLK1 gene is shown in SEQ ID NO:1.

Step 2. the above system was transferred to a 4° C. environment, acrylate polyethylene glycol succinimidyl formate was added and stirred for 10 minutes, then guanidino acrylate was added and stirred for 5 minutes, and then the degradable N,N'-bis(acryloyl)cystamine was added, wherein the molar ratio of acrylate polyethylene glycol succinimidyl formate, guanidino acrylate, and N,N'-bis(acryloyl)cystamine was 1:1:1. 3 mg of ammonium persulfate and 3 µL of N,N, N',N'-tetramethylethylenediamine solution were added to immediately initiate the polymerization reaction, wherein the polymerization reaction was carried out at 4° C. and under nitrogen protection for 90 minutes, the polymerization reaction process was always accompanied by mechanical stirring.

Specifically, the molar ratio of the Cas nuclease and the guanidino acrylate was 1:220.

Step 3. the amination-treated Angiopep-2 was added to the above system, stirred at room temperature for 2 hours, thereby finally forming the nanocapsules.

Specifically, in both step 2 and step 3, a magnetic stirrer was used for stirring, and the stirring speed was 250-350 rpm.

Step 4. a centrifugal filter tube with a 10 kDa molecular weight cut-off is used for impurity removal to remove unreacted monomers and initiators, PBS buffer (pH 7.4) is used to dilute the concentrated solution.

Figure 1B:
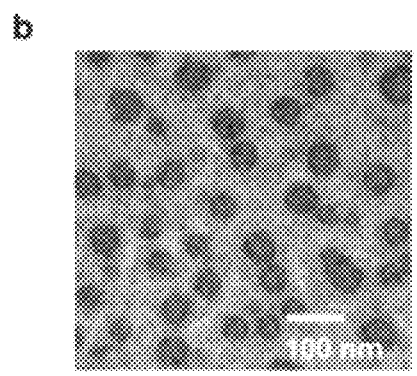

FIG. 1A and FIG. 1B are views of DLS test results of $ANC_{SS}$ (Cas9/sgRNA) nanocapsules prepared in Example 1. As shown in FIG. 1A and FIG. 1B, the average particle size of the nanocapsules prepared in Example 1 is 31 nm, and the particle size distribution is relatively uniform.

Example 2 Preparation Method of $ANC_{SS}$ (Cas9/sgRNA) Nanocapsules

The difference from Example 1 above is only that: the molar ratio of the Cas nuclease and the guanidino acrylate was 1:200.

Example 3 Preparation Method of $ANC_{SS}$ (Cas9/sgRNA) Nanocapsules

The difference from Example 1 above is only that: the molar ratio of the Cas nuclease and the guanidino acrylate was 1:250.

Comparative Example 1 Preparation Method of ANC (Cas9/sgRNA) Nanocapsules

The difference from Example 1 above is only that: in the step 2, hexamethylene diacrylate that cannot be degraded by GSH was used to replace N, N'-bis(acryloyl) cystamine that can be degraded by GSH, therefore, the polymers in the prepared ANC (Cas9/sgRNA) nanocapsules cannot be specifically degraded by tumor cells, thus the gene editing system (Cas9RNP) in the ANC (Cas9/sgRNA) nanocapsule cannot be efficiently released in tumor cells, the gene editing efficiency is lower.

Comparative Example 2 Preparation Method of $NC_{SS}$ (Cas9/sgRNA) Nanocapsules

The difference from Example 1 above is that: step 3 was not included (that is, Angiopep-2 was not added), and at the same time the acrylate polyethylene glycol succinimidyl formate was replaced with methoxy polyethylene glycol amine (mPEG-$NH_2$) MW: 2000 (purchased from Ponsure), and the prepared $NC_{SS}$ (Cas9/sgRNA) nanocapsules do not have the ability of spanning BBB and cannot be efficiently swallowed by human glioma cells.

Comparative Example 3 Preparation Method of $ANC_{SS}$ (Cas9/sgScr) Nanocapsules The difference from Example 1 above is only that: the sgRNA used in Comparative Example 3 was an invalid sgRNA, which does not have a targeting function.

Comparative Example 4 Preparation Method of Free Cas9/sgRNA

Cas9 and sgRNA were added to 500 µl HEPES buffer at a molar ratio of 1:1.2, and incubated for 5 minutes at room temperature.

It is worth mentioning that the $ANC_{SS}$ (Cas9/sgRNA) nanocapsules used in the following (2) cell experiment and (3) animal experiment were all the nanocapsules prepared in Example 1, ANC (Cas9/sgRNA) nanocapsule was prepared from Comparative Example 1, $NC_{SS}$ (Cas9/sgRNA) nanocapsule was prepared from Comparative Example 2, $ANC_{SS}$ (Cas9/sgScr) nanocapsule was prepared from Comparative Example 3, and Free Cas9/sgRNA was prepared from Comparative Example 4.

(2) Cell Experiment

① Cell Endocytosis and Intracellular Release were Characterized by a Flow Cytometry and a Confocal Microscope In the flow cytometry test, after U87MG-luc cells were inoculated in a 6-well cell culture plate ($1\times10^6$ cells/well) and cultured at 37°C for 24 hours, 150 μL PBS solution (Cas9 concentration was 20 nM) of $ANC_{SS}$ (Cas9/sgRNA) nanocapsules, ANC (Cas9/sgRNA) nanocapsules, $NC_{SS}$ (Cas9/sgRNA) nanocapsules, and Free Cas9/sgRNA was added and incubated for 4 hours, the sample was sucked out, and the cells were digested with 500 μL trypsin. The obtained cell suspension was centrifuged at 1000×g for 3 minutes, washed twice with PBS buffer, and dispersed in 500 μL PBS buffer again, and tested by the flow cytometry (BD FACS Calibur, Becton Dickinson, USA) within 1 hour, Cell Quest software was used to circle 10,000 cells to obtain them.

The cell endocytosis and intracellular drug release behavior were observed and obtained through CLSM (Confocal laser scanning microscope) photos. After U87MG-luc cells were spread in a 24-well cell culture plate ($1\times10^5$ cells/well) containing microscope slides to culture for 24 hours, 50 μL PBS buffer (Cas9 concentration was 20 nM) of $ANC_{SS}$ (Cas9/sgRNA) nanocapsules, ANC (Cas9/sgRNA) nanocapsules, $NC_{SS}$ (Cas9/sgRNA) nanocapsules, and Free Cas9/sgRNA were added. After incubating for 4 hours, the culture medium was removed and the resultant was washed twice with PBS buffer. The cytoskeleton was stained with Phalloidin for 30 minutes and washed twice, and then the nucleus was stained with DAPI for 15 minutes and washed twice. The fluorescence picture was taken by CLSM (TCS SP5).

② Editing Efficiency of Cells was Characterized by an In Vitro Gene Editing

Figure 2A:
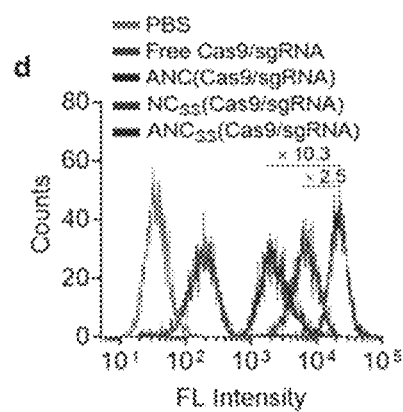
Figure 2B:
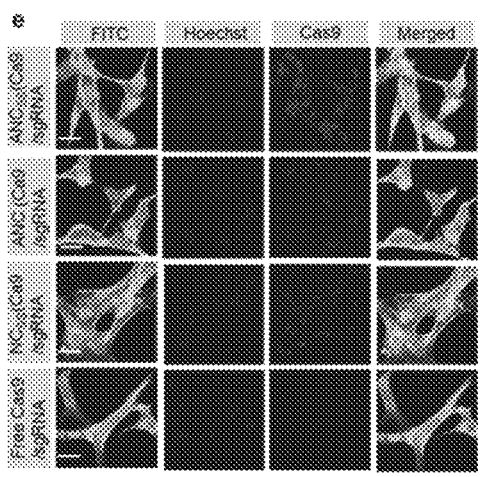
Figure 2C:
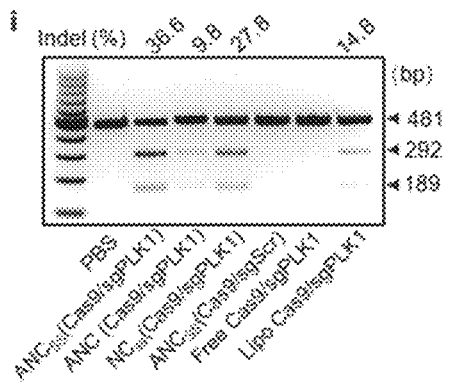
Figure 2D:
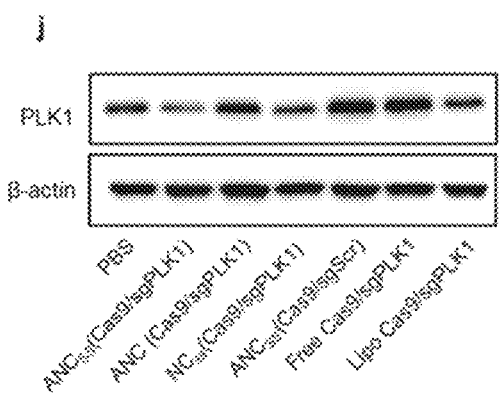
Figure 2E:
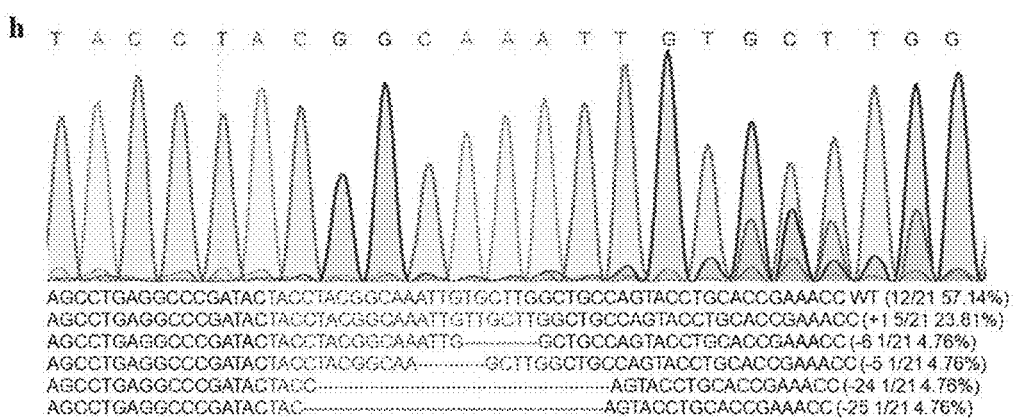
Figure 3A:
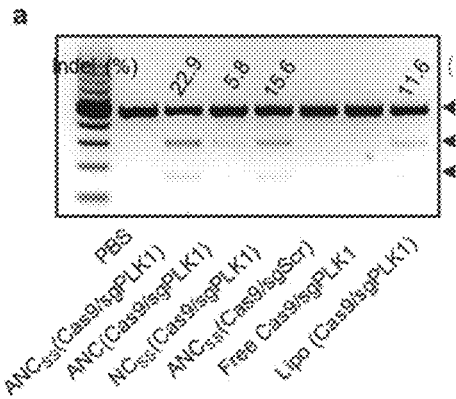
FIG. 3A and FIG. 3B show the experiment results of another part of in vitro cells, wherein FIG. 3A T7E1 experiment analyzes the editing efficiency in CSC2-luc cells, and the values are obtained by imageJ analysis.
Figure 3B:
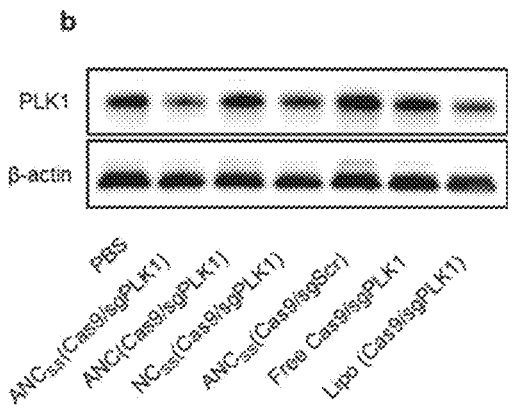

U87MG-luc/CSC2-luc cells were inoculated in a 24-well plate ($5\times10^4$ cells/well) and cultured for 24 hours. 50 μL PBS solution (Cas9 concentration was 20 nM) of $ANC_{SS}$ (Cas9/sgRNA) nanocapsules, $ANC_{SS}$ (Cas9/sgScr) nanocapsules, ANC (Cas9/sgRNA) nanocapsules, $NC_{SS}$ (Cas9/sgRNA) nanocapsules, and Free Cas9/sgRNA was added and incubated overnight, and then culture medium was replaced, the cells were incubated again at 37°C for 48 h. Universal genomic DNA kit (China, CWBIO) was used to extract genomic DNA. Then, the high-fidelity enzyme Kod-Plus-Neo (Japan, TOYOBO) was used to amplify the DNA fragment containing the sgRNA target site, and the PCR products were purified by the gel recovery kit (CWBIO, China). Finally, T7E1 enzyme (USA, NEB) detected insertion and deletion efficiency. The PCR products with T7E1 analysis indicating mutations were performed by DNA sequencing, and then subcloned into T cloning vector (Vazyme Biotech, China). Colonies were randomly selected and further analyzed by DNA Sanger sequencing using M13F as a primer (Sangon Biotech), the sequencing results of some clones are shown in FIG. 2E. Sanger sequencing results showed that 12 out of 21 clones had mutations in the target sequence, wherein the mutation type of 5 clones was T single base insertion, and the mutation type of 7 clones was base deletion.

③ Protein Expression Level in Cells was Characterized by In Vitro WB Experiment

U87MG-luc/CSC2-luc cells were inoculated in a 6-well plate ($1\times10^5$ cells/well) and cultured for 24 hours. 150 μL PBS solution (Cas9 concentration was 20 nM) of $ANC_{SS}$ (Cas9/sgRNA) nanocapsules, $ANC_{SS}$ (Cas9/sgScr) nanocapsules, ANC (Cas9/sgRNA) nanocapsules, $NC_{SS}$ (Cas9/sgRNA) nanocapsules, and Free Cas9/sgRNA was added and incubated overnight, and then culture medium was replaced, the cells were incubated again at 37° C. for 72 h. The cells were treated with lysis buffer (Beyotime, China), and the concentration of the obtained protein was quantified by the BCA kit (Beyotime, China). The lysate was separated by electrophoresis (SDS polyacrylamide gel) and transferred to PDVF membrane (Beyotime, China). The PDVF membrane and the anti-PLK1 primary antibody (mouse mAb 35-206, Abcam) were diluted at 1:1000 and incubated overnight at 4°C. The resultant was incubated for 1 h with ECL secondary antibody, showing protein bands (Licor, USA). Protein bands were analyzed by using ImageJ software.

(3) Animal Experiment

① Pharmacokinetic Study

In the in vivo pharmacokinetic study, 6-8 weeks BALB/c mice were randomly divided into groups (3 mice in each group), 200 μL of $ANC_{SS}$ (Cas9/sgRNA) nanocapsules, ANC (Cas9/sgRNA) nanocapsules, $NC_{SS}$ (Cas9/sgRNA) nanocapsules, and Free Cas9/sgRNA (Cas9 dosage was 30 μg) were injected to the tail vein, blood was taken from the eye socket at a predetermined time point. The drug was extracted and separated from the blood sample by organic solvent, and quantified by a multimode reader. Pharmacokinetic parameters such as elimination half-life of drug in the body (t1/2), area under the drug concentration-time curve (AUC), clearance rate (CL) can be calculated by software fitting.

② Anti-Tumor Effect

U87MG-Luc or CSC2-Luc glioma orthotopic model was established by transplanting tumor tissue into the brain of BALB/c nude mice (18-20 g, 6-8 weeks old). When the tumor volume was 20-30 $mm^3$, it was used for treatment experiments; when the tumor volume was 100-150 $mm^3$, it was used for biodistribution experiments.

Orthotopic model was established by luciferase-marked human glioma cell U87MG-Luc or human glioma stem cell CSC2-Luc, single-dose or multiple-dose administration was achieved through tail vein injection method, the tumor growth was tracked qualitatively and quantitatively by IVIS III. In the course of treatment, the systemic toxic and side effects and anti-tumor activity of nanomedicine were evaluated by the weight change and survival rate of mice. After the treatment was finished, the health status of normal organs and apoptosis condition of the tumor tissue in mice after nanomedicine treatment were analyzed through the histological staining methods such as H&E and TUNEL. Through treatment experiments, the systemic toxicity and the anti-tumor activity of the nanomedicine on U87MG-Luc or CSC2-Luc tumor-bearing nude mice can be determined.

③ Biodistribution

The nanomedicine was injected into the body of nude mice bearing orthotopic U87MG-luc/CSC2-Luc through the tail vein, and heart, liver, spleen, lung, kidney, brain and tumors and other major tissues of mice were collected at different time points, which were imaged in vitro by IVIS III. Subsequently, after each tissue was homogenized, extracted by the organic solvent and separated by centrifuging to obtain the supernatant, fluorescence spectrophotometer quantitatively analyzed the biodistribution of drug in the body at different time points. Through this experiment, the in vivo stability of nanomedicine, active targeting performance and the effect of enrichment, retention, and penetration of the released Cas9 drug on the tumor site can be known.

④ BBB Spanning Effect and Targeting

The nanomedicine was injected into the body of nude mice bearing orthotopic human glioma U87MG-luc through the tail vein, and the distribution of nanomedicine at different time points in the body was tracked by the small animal imager (IVIS III), the accumulation and retention of brain tumor sites were focused on, and by qualitative and quantitative comparison with the non-targeting control group ($NC_{SS}$ (Cas9/sgRNA) nanocapsules) and the non-sensitive control group (ANC (Cas9/sgRNA) nanocapsules), the BBB spanning efficiency and the tumor targeting ability of nanomedicine were investigated.

(4) Results and Discussion (1) In Vitro Cell Experiment

Flow cytometry experiments (FIG. 2A) proved that $ANC_{SS}$ (Cas9/sgRNA) nanocapsules have very high cell endocytosis efficiency, and the cell endocytosis efficiency thereof is 2.5 times that of the non-targeting control group $NC_{SS}$ (Cas9/sgRNA), and 10.3 times that of the control group ANC (Cas9/sgRNA).

CLSM (confocal laser scanning microscope) (FIG. 2B) observed that after $ANC_{SS}$ (Cas9/sgRNA) nanocapsules were incubated for 4 hours, there was strong Cas9 fluorescence in the U87MG-luc nucleus, which confirmed that $ANC_{SS}$ (Cas9/sgRNA) nanocapsule can be quickly degraded in cell to release Cas9, which is transported to the nucleus to function.

In vitro gene editing experiments (FIG. 2C) proved that $ANC_{SS}$ (Cas9/sgRNA) nanocapsules have a very high gene editing efficiency for U87MG-luc cells, reaching 36.6%.

WB experiments (FIG. 2D) proved that $ANC_{SS}$ (Cas9/sgRNA) nanocapsules can significantly reduce the expression of PLK1 in U87MG-luc cells, thereby achieving the effect of inhibiting tumor growth.

Figure 4A:
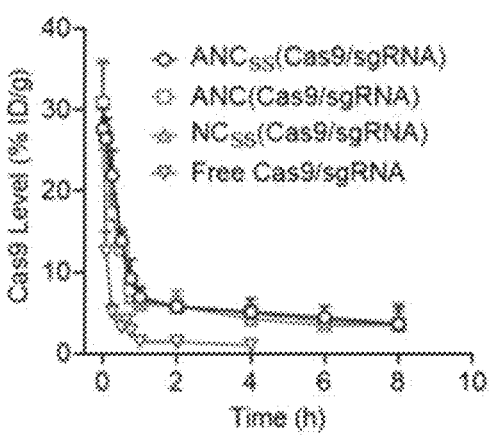

(2) In Vivo Experimental Study on the Pharmacokinetics and Biodistribution of Targeting Nanomedicine $ANC_{SS}$ (Cas9/sgRNA) Nanocapsules In vivo pharmacokinetics (FIG. 4A) study results showed that the targeting nanomedicine $ANC_{SS}$ (Cas9/sgRNA) has a longer circulation time in the body, which is equivalent to that of ANC (Cas9/sgRNA) nanocapsule and $NC_{SS}$ (Cas9/sgRNA) nanocapsule, and significantly longer than that of Free Cas9/sgRNA, which showed that the biocompatibility of nanocapsules is better.

Figure 4B:
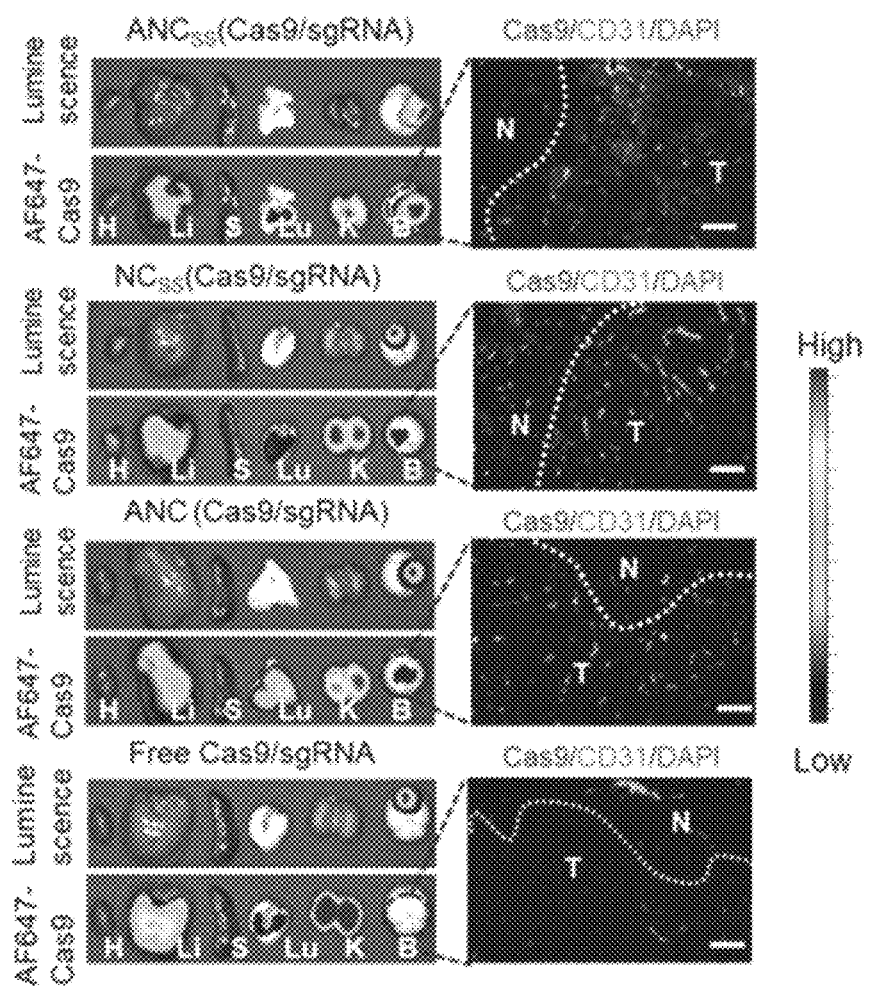
Figure 4C:
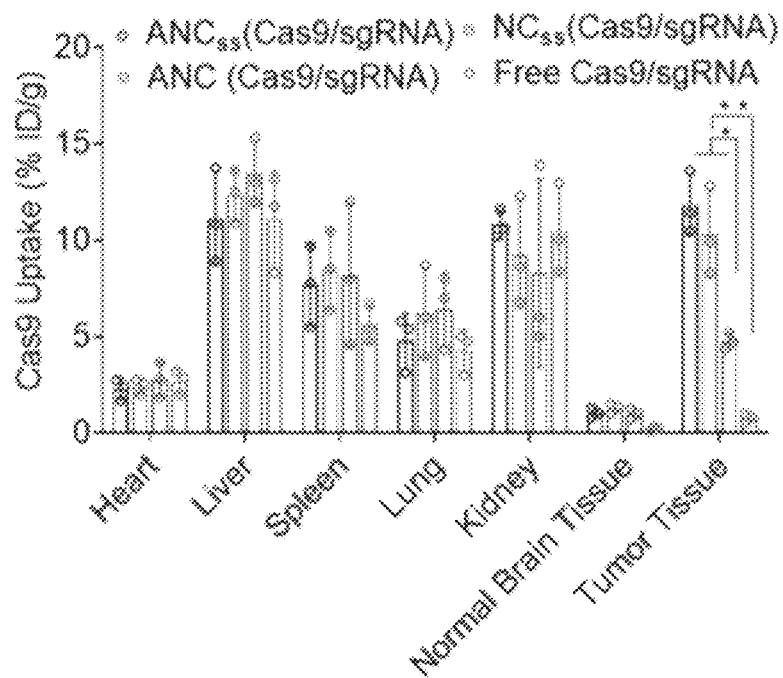
Figure 5A:
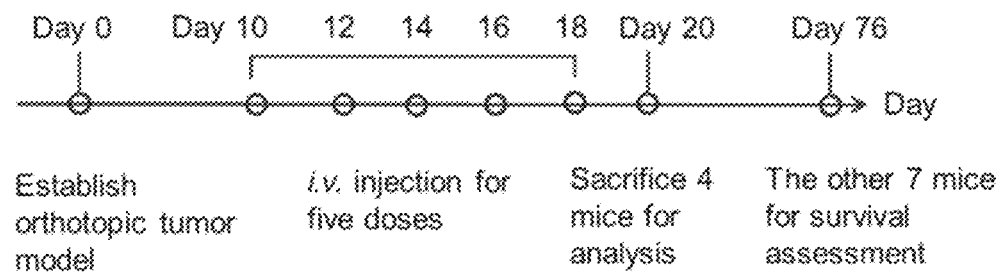
FIG. 5A-FIG. 5J shows the in vivo therapeutic effect of ANC$_{SS}$ (Cas9/sgRNA) nanocapsules on U87MG-luc tumor-bearing mice, wherein FIG. 5A schematic view showing in situ tumor study timetable.
Figure 5B:
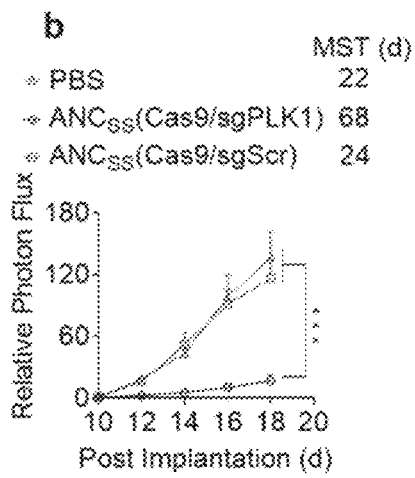
Figure 5C:
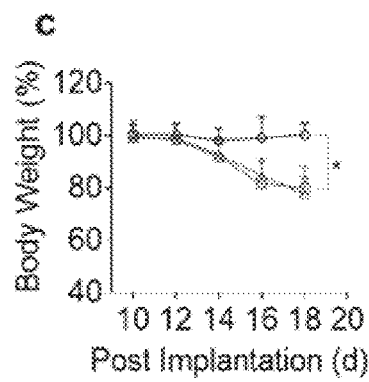
Figure 5D:
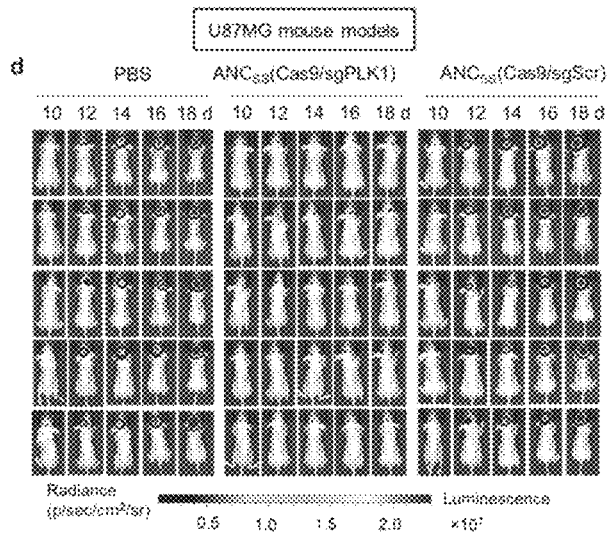
Figure 5E:
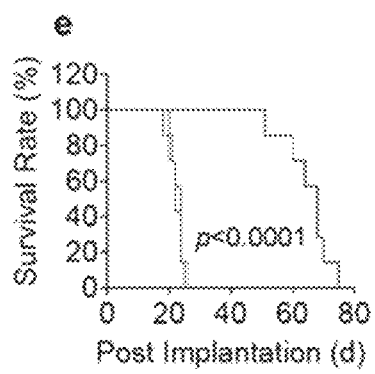
Figure 5F:
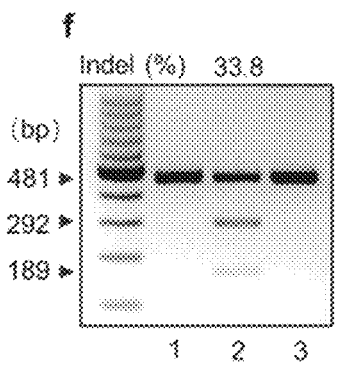
Figure 5G:
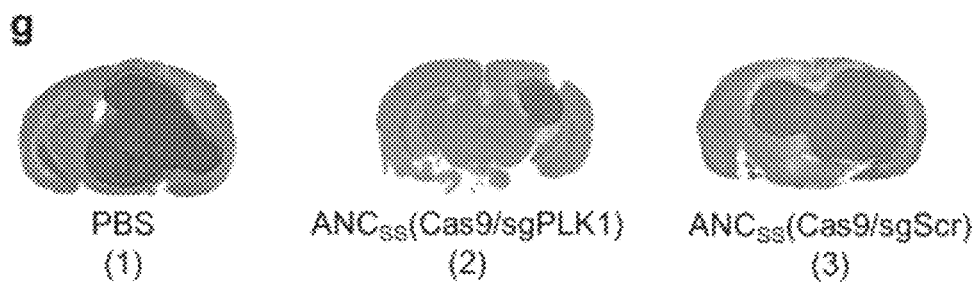
Figure 5H:
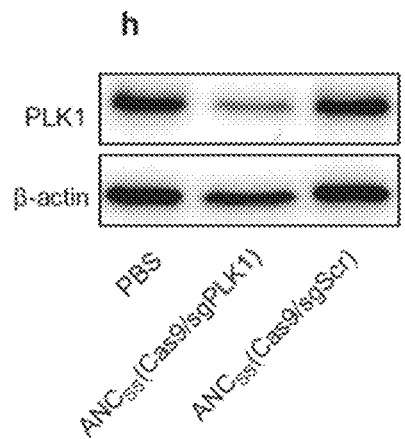
Figure 5I:
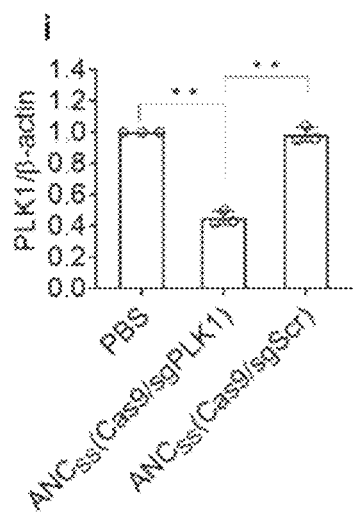
Figure 5J:
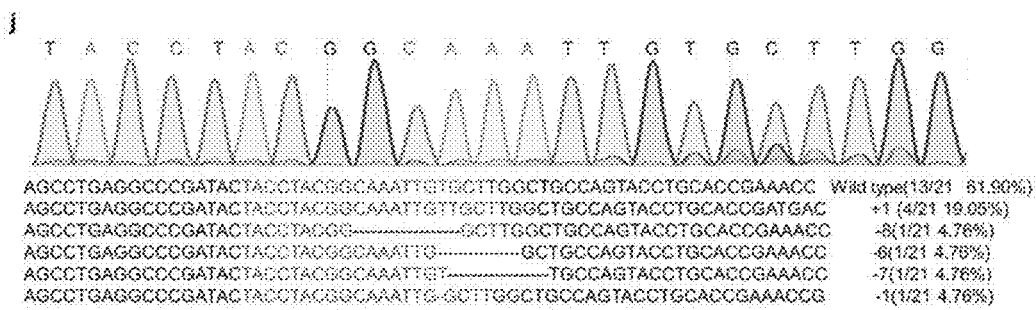
Figure 6A:
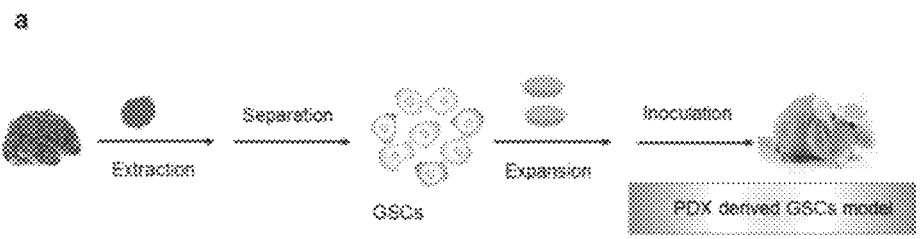
FIG. 6A-FIG. 6J shows the in vivo therapeutic effect of ANC$_{SS}$ (Cas9/sgRNA) nanocapsules on CSC2-luc tumor-bearing mice, wherein FIG. 6A schematic view of establishment of the PDX derived GBM GSC orthotopic model.
Figure 6B:
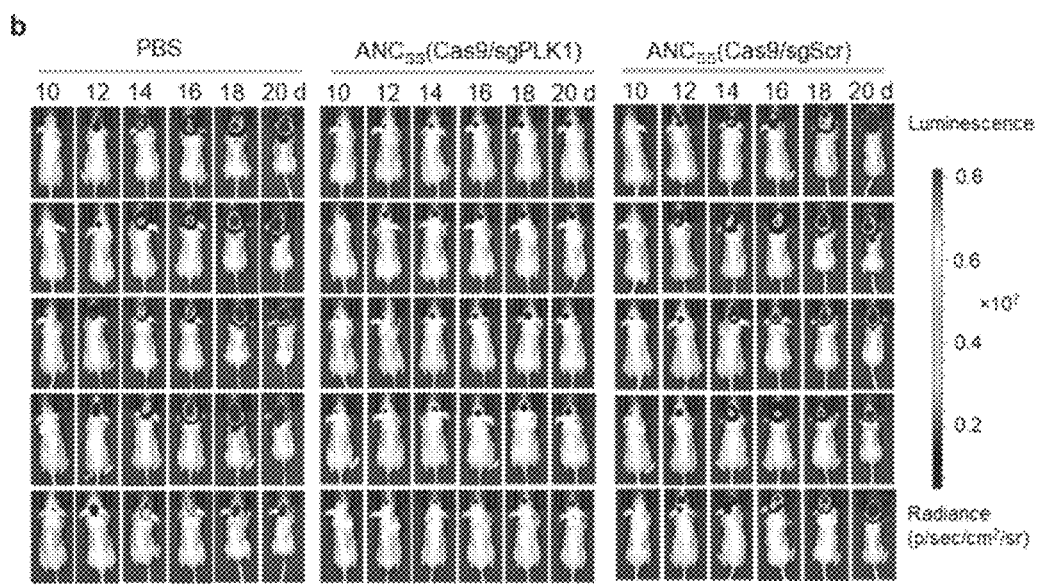
Figure 6C:
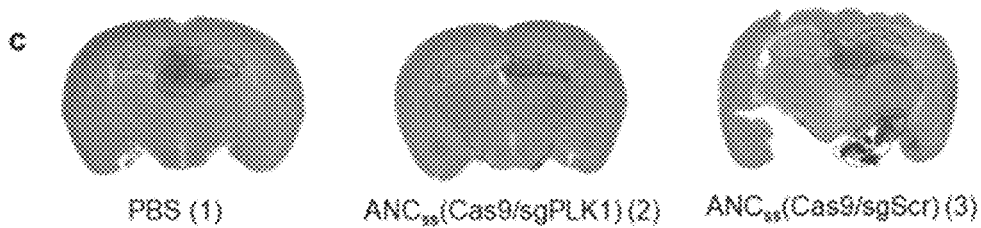
Figure 6D:
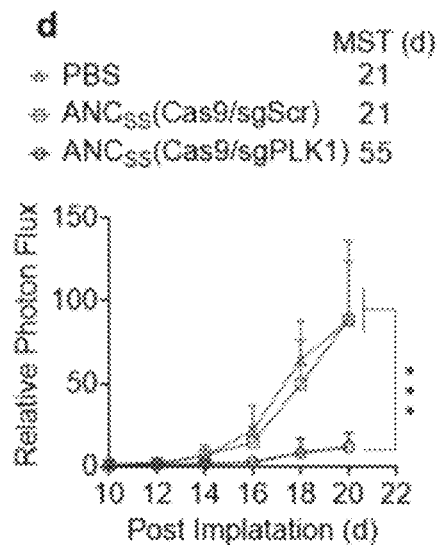
Figure 6E:
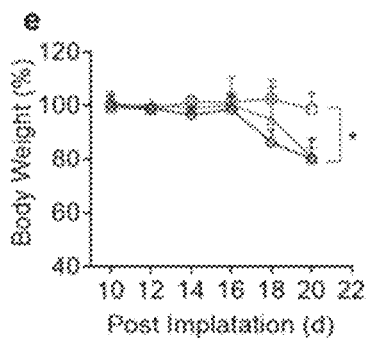
Figure 6F:
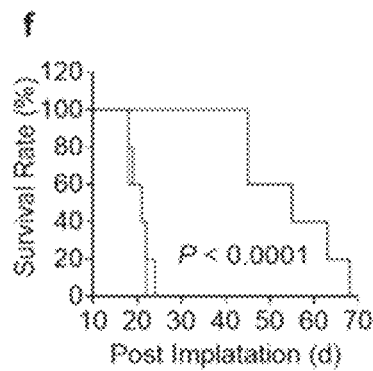
Figure 6G:
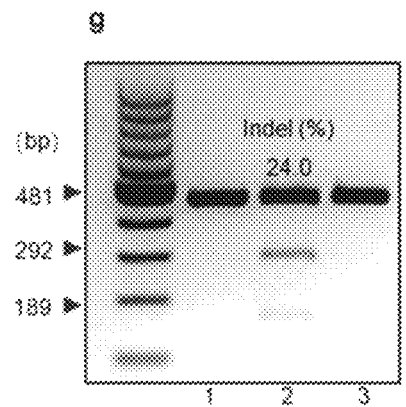
Figure 6H:
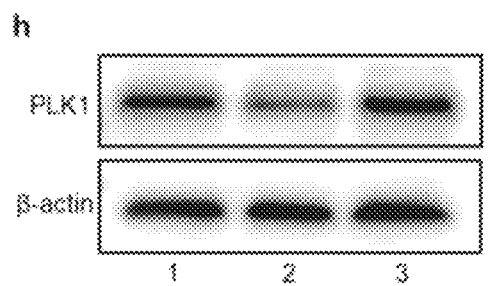
Figure 6I:
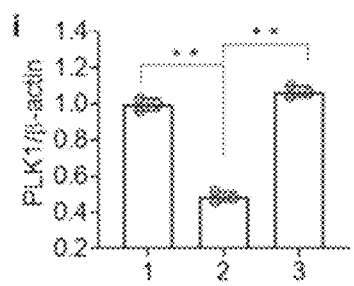
Figure 6J:
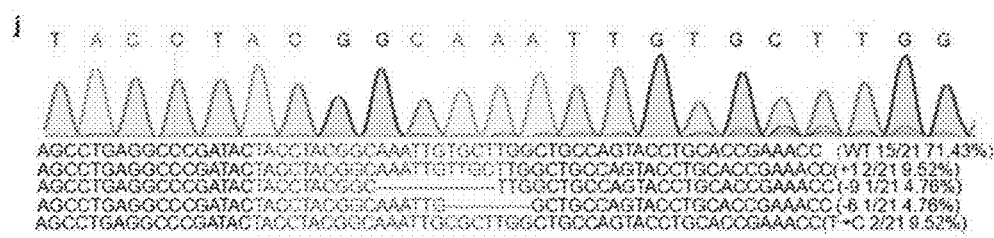

In vivo biodistribution experiment (FIG. 4B, FIG. 4C) results of BALB/c mice bearing U87MG-luc glioma showed that the enrichment amount of $ANC_{SS}$ (Cas9/sgRNA) nanocapsules at the tumor site is significantly higher than that of Free Cas9/sgRNA, 4 hours after injection, the enrichment amount of Cas9 is 12% (the content of Cas9 in each gram of tissue accounts for the mass percentage of the total injection volume).

(3) Anti-Tumor Experiment and Histological Analysis of $ANC_{SS}$ (Cas9/sgRNA) Nanocapsules The treatment experimental results of $ANC_{SS}$ (Cas9/sgRNA) nanocapsules in U87MG-luc tumor-bearing BALB/c nude mice are shown in FIG. 5A-FIG. 5J.

In FIG. 5A-FIG. 5J, $ANC_{SS}$ (Cas9/sgPLK1) indicates that the target gene of sgRNA is PLK1, $ANC_{SS}$ (Cas9/sgScr) indicates a negative control experiment, and PBS indicates PBS buffer (control experiment).

It can be seen from FIG. 5A-FIG. 5J that $ANC_{SS}$ (Cas9/sgRNA) nanocapsules can effectively inhibit tumor growth. The weight of the mice treated with $ANC_{SS}$ (Cas9/sgRNA) nanocapsules changed slightly, in comparison, the body weight of the PBS group decreased by 20% within 8 days, which shows that $ANC_{SS}$ (Cas9/sgRNA) nanocapsules have little toxic and side effects, in addition, those skilled in the art have known that the growth of brain tumors can cause weight loss, therefore, the experimental data of the present disclosure reflects that $ANC_{SS}$ (Cas9/sgRNA) nanocapsules have a better curative effect and can inhibit brain tumors.

The treatment experimental results of $ANC_{SS}$ (Cas9/sgRNA) nanocapsules in CSC2-luc tumor-bearing BALB/c nude mice are shown in FIG. 6A-FIG. 6J.

In FIG. 6A-FIG. 6J, $ANC_{SS}$ (Cas9/sgPLK1) indicates that the target gene of sgRNA is PLK1, $ANC_{SS}$ (Cas9/sgScr) indicates a negative control experiment, and PBS indicates PBS buffer (control experiment).

It can be seen from FIG. 6A-FIG. 6J that $ANC_{SS}$ (Cas9/sgRNA) nanocapsules can effectively inhibit tumor growth. The weight of the mice treated with $ANC_{SS}$ (Cas9/sgRNA) nanocapsules changed slightly, which shows that $ANC_{SS}$ (Cas9/sgRNA) nanocapsules have little toxic and side effects, in addition, those skilled in the art have known that the growth of brain tumors can cause weight loss, therefore, the experimental data of the present disclosure reflects that $ANC_{SS}$ (Cas9/sgRNA) nanocapsules have a better curative effect and can inhibit brain tumors.

What is striking is that after the mice were treated with an $ANC_{SS}$ (Cas9/sgRNA) nanocapsule dosage of 30 μg, the survival cycle was significantly prolonged. The histological analysis results by H&E staining proved that after treatment with $ANC_{SS}$ (Cas9/sgRNA) nanocapsules at a dosage of 30 μg, there is little harm to major organs including the heart, liver, spleen, lung, and kidney. The results once again show that $ANC_{SS}$ (Cas9/sgRNA) nanocapsules have extremely low systemic toxicity.

(4) Tumor Targeting Experiment of $ANC_{SS}$ (Cas9/sgRNA) Nanocapsules

Figure 7:
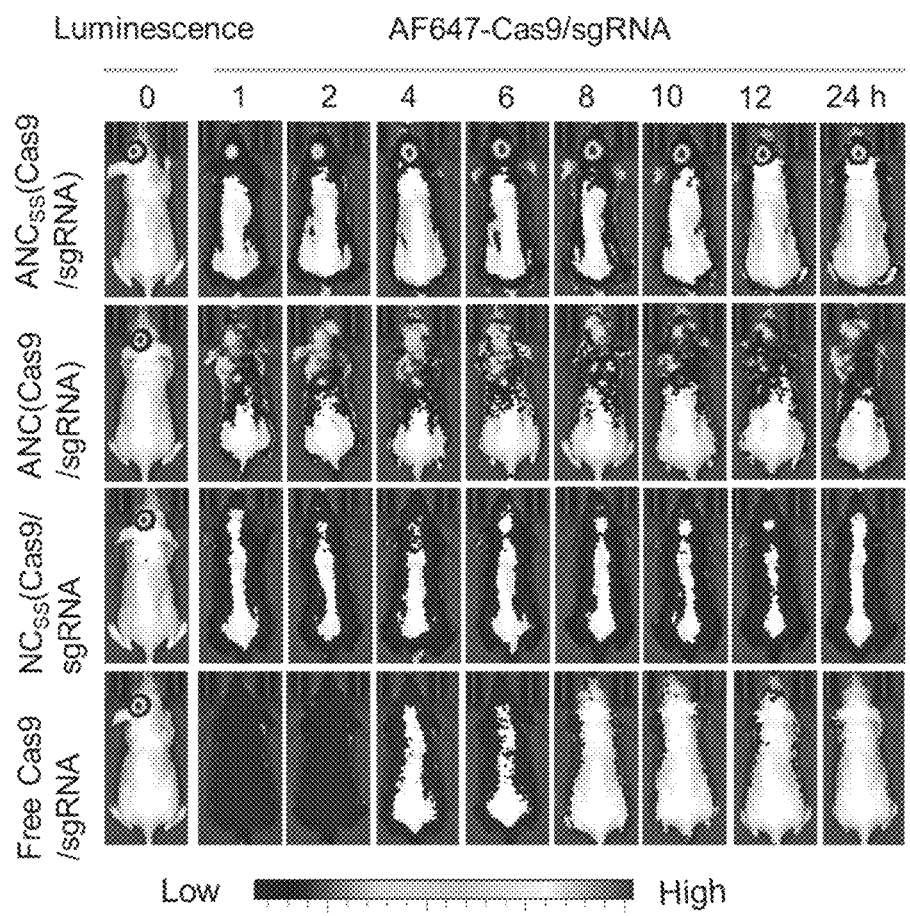
FIG. 7 shows the fluorescence intensity at different time points after ANC$_{SS}$ (Cas9/sgRNA) nanocapsules, ANC (Cas9/sgRNA) nanocapsules, NC$_{SS}$ (Cas9/sgRNA) nanocapsules, and Free Cas9/sgRNA were injected into mice.

The results of tracking the distribution (FIG. 7) of nanomedicine in the body at different time points by the small animal imager (IVIS III) showed that the fluorescence intensity of $ANC_{SS}$ (Cas9/sgRNA) nanocapsule is significantly higher than that of the control group, which indicates that it has a very good ability of targeting tumors.

Finally, it should be noted that the above embodiments are only used to illustrate the technical solutions of the present disclosure, not to limit them; although the present disclosure has been described in detail with reference to the foregoing embodiments, those ordinary skilled in the art should understand that: the technical solutions recorded in the foregoing embodiments can still be modified, or some or all of the technical features therein can be equivalently replaced; and these modifications or replacements do not make the essence of the corresponding technical solutions deviate from the scope of technical solutions of the embodiments of the present disclosure.

In addition, those skilled in the art can understand that although some embodiments herein include certain features included in other embodiments but not other features, the combination of features of different embodiments means that they fall within the scope of the present disclosure and form different embodiments. For example, in the claims, any one of the claimed embodiments can be used in any combination. The information disclosed in the background section is only intended to deepen the understanding of the overall background of the present disclosure, and should not be regarded as an acknowledgement or any form of suggestion that the information constitutes the prior art already known to those skilled in the art.

What is claimed is:

1. A gene editing nanocapsule, comprising an inner core and an outer shell encapsulating the inner core, wherein the inner core comprises a Cas/sgRNA ribonucleoprotein complex obtained by combining Cas nuclease and sgRNA, wherein the Cas nuclease is Cas9 nuclease, and a molar ratio of the Cas nuclease and the sqRNA is 1:1.2; and the outer shell comprises a polymer polymerized by a monomer material, wherein the monomer material comprises a first monomer and a second monomer that can be polymerized capable of polymerizing with each other, wherein the first monomer is guanidino acrylate and the second monomer is N,N'-bis(acryloyl)cystamine, and a molar ratio of the Cas nuclease and the guanidino acrylate is 1:200-250.

2. The gene editing nanocapsule according to claim 1, wherein the gene editing nanocapsule further comprises a targeting agent modified on an outer surface of the outer shell; the monomer material further comprises a third monomer capable of polymerizing with the first monomer and/or the second monomer, wherein the third monomer is a molecule capable of connecting to the targeting agent through a chemical bond.

3. The gene editing nanocapsule according to claim 1, wherein a target gene of the sgRNA is a tumor-targeted therapeutic gene.

4. The gene editing nanocapsule according to claim 2, wherein the targeting agent is Angiopep-2.

5. A drug for treating a tumor, comprising the gene editing nanocapsule according to claim 1.

6. A preparation method for the gene editing nanocapsule according to claim 1, comprising the following steps: step 1: incubating Cas nuclease and sgRNA in a buffer to form the Cas/sgRNA ribonucleoprotein complex; and step 2: adding the monomer material and an initiator to the Cas/sgRNA ribonucleoprotein complex obtained in step 1, so that the monomer material undergoes a polymerization reaction to form the polymer that is coated on an outer surface of the Cas/sgRNA ribonucleoprotein complex, thereby producing the gene editing nanocapsule.

7. The preparation method for the gene editing nanocapsule according to claim 6, wherein the preparation method further comprises: step 3: adding a targeting agent to the gene editing nanocapsule obtained in step 2, wherein the targeting agent is connected to the polymer by a chemical bond; and the monomer material added in step 2 further comprises a third monomer capable of polymerizing with the first monomer and/or the second monomer, wherein the third monomer is a molecule capable of connecting to the targeting agent through a chemical bond.

8. The preparation method for the gene editing nanocapsule according to claim 6, wherein the initiator comprises ammonium persulfate and N,N,N',N'-tetramethylethylenediamine, wherein a ratio of the ammonium persulfate and polymerization reaction solution is 1-5 mg:500 µL, a ratio of a N,N,N',N'-tetramethylethylenediamine solution and the polymerization reaction solution is, 1-5 µL:500 µL and a concentration of the N,N,N',N'-tetramethylethylenediamine solution is 0.2%-0.8% w/v.

9. The gene editing nanocapsule according to claim 2, wherein the targeting agent comprises at least one of Angiopep-2, RGD peptide, apolipoprotein E, and transferrin.

10. The gene editing nanocapsule according to claim 3, wherein the tumor-targeted therapeutic gene comprises at least one of a MTH1 gene and a PLK1 gene.

11. The gene editing nanocapsule according to claim 10, wherein a sequence of a target site of the sgRNA on the PLK1 gene is the nucleotide sequence of SEQ ID NO:1.

12. The drug for treating a tumor according to claim 5, wherein the tumor is glioma, non-small cell lung cancer or cervical cancer.

13. The preparation method for the gene editing nanocapsule according to claim 7, wherein in step 3, after adding the targeting agent, stirring is carried out for 1 to 3 hours.

14. The preparation method for the gene editing nanocapsule according to claim 7, wherein the third monomer comprises at least one of acrylate polyethylene glycol succinimidyl formate and acrylate polyethylene glycol maleimide.

15. The preparation method for the gene editing nanocapsule according to claim 8, wherein the step 1 is performed under a condition of 10° C.-30° C., and an incubation time is 3 to 8 minutes; and the step 2 is performed at 0° C.-5° C. in an oxygen-free environment with stirring, and a reaction time is 60 to 120 minutes.

16. The preparation method for the gene editing nanocapsule according to claim 8, wherein the preparation method for the gene editing nanocapsule further comprises: performing a step of removing impurities after the gene editing nanocapsule are is prepared.

17. The preparation method for the gene editing nanocapsule according to claim 16, wherein an ultrafiltration centrifuge tube with a 10 kDa molecular weight cut-off is used for removing impurities.

\* \* \* \* \*

SEQUENCE LISTING

<160> NUMBER OF SEQ ID NOS: 13

<210> SEQ ID NO 1
<211> LENGTH: 20
<212> TYPE: DNA
<213> ORGANISM: Homo sapiens
<400> SEQUENCE: 1
tacctacggc aaattgtgct                                            20

<210> SEQ ID NO 2
<211> LENGTH: 63
<212> TYPE: DNA
<213> ORGANISM: Mus musculus
<400> SEQUENCE: 2
agcctgaggc ccgatactac ctacggcaaa ttgtgcttgg ctgccagtac ctgcaccgaa    60
acc                                                              63

<210> SEQ ID NO 3
<211> LENGTH: 64
<212> TYPE: DNA
<213> ORGANISM: Mus musculus
<400> SEQUENCE: 3
agcctgaggc ccgatactac ctacggcaaa ttgttgcttg gctgccagta cctgcaccga    60
aacc                                                             64

<210> SEQ ID NO 4
<211> LENGTH: 57
<212> TYPE: DNA
<213> ORGANISM: Mus musculus
<400> SEQUENCE: 4
agcctgaggc ccgatactac ctacggcaaa ttggctgcca gtacctgcac cgaaacc        57

<210> SEQ ID NO 5
<211> LENGTH: 58
<212> TYPE: DNA
<213> ORGANISM: Mus musculus
<400> SEQUENCE: 5
agcctgaggc ccgatactac ctacggcaag cttggctgcc agtacctgca ccgaaacc       58

<210> SEQ ID NO 6
<211> LENGTH: 39
<212> TYPE: DNA
<213> ORGANISM: Mus musculus
<400> SEQUENCE: 6
agcctgaggc ccgatactac cagtacctgc accgaaacc                         39

<210> SEQ ID NO 7
<211> LENGTH: 38
<212> TYPE: DNA
<213> ORGANISM: Mus musculus
<400> SEQUENCE: 7
agcctgaggc ccgatactac agtacctgca ccgaaacc                           38

<210> SEQ ID NO 8
<211> LENGTH: 64

```
<212> TYPE: DNA
<213> ORGANISM: Mus musculus

<400> SEQUENCE: 8
agcctgaggc ccgatactac ctacggcaaa ttgttgcttg gctgccagta cctgcaccga    60
tgac                                                                 64

<210> SEQ ID NO 9
<211> LENGTH: 55
<212> TYPE: DNA
<213> ORGANISM: Mus musculus

<400> SEQUENCE: 9
agcctgaggc ccgatactac ctacgggctt ggctgccagt acctgcaccg aaacc         55

<210> SEQ ID NO 10
<211> LENGTH: 56
<212> TYPE: DNA
<213> ORGANISM: Mus musculus

<400> SEQUENCE: 10
agcctgaggc ccgatactac ctacggcaaa ttgttgccag tacctgcacc gaaacc        56

<210> SEQ ID NO 11
<211> LENGTH: 63
<212> TYPE: DNA
<213> ORGANISM: Mus musculus

<400> SEQUENCE: 11
agcctgaggc ccgatactac ctacggcaaa ttggcttggc tgccagtacc tgcaccgaaa    60
ccg                                                                  63

<210> SEQ ID NO 12
<211> LENGTH: 54
<212> TYPE: DNA
<213> ORGANISM: Mus musculus

<400> SEQUENCE: 12
agcctgaggc ccgatactac ctacggcttg gctgccagta cctgcaccga aacc          54

<210> SEQ ID NO 13
<211> LENGTH: 63
<212> TYPE: DNA
<213> ORGANISM: Mus musculus

<400> SEQUENCE: 13
agcctgaggc ccgatactac ctacggcaaa ttgcgcttgg ctgccagtac ctgcaccgaa    60
acc                                                                  63
```